United States Patent
Wheaton et al.

(10) Patent No.: US 11,007,135 B2
(45) Date of Patent: May 18, 2021

(54) LIQUID COSMETIC

(71) Applicant: Parfums de Coeur, Ltd., Stamford, CT (US)

(72) Inventors: Randy M Wheaton, Danbury, CT (US); Yewei Wang, Shanghai (CN)

(73) Assignee: Parfums de Coeur, Ltd., Stamford, CT (US)

(*) Notice: Subject to any disclaimer, the term of this patent is extended or adjusted under 35 U.S.C. 154(b) by 0 days.

(21) Appl. No.: 16/426,358

(22) Filed: May 30, 2019

(65) Prior Publication Data

US 2020/0360263 A1    Nov. 19, 2020

(30) Foreign Application Priority Data

May 13, 2019 (CN) .......................... 201910393434.5

(51) Int. Cl.
*A61K 8/81* (2006.01)
*A61K 8/19* (2006.01)
*A61Q 1/10* (2006.01)

(52) U.S. Cl.
CPC .............. *A61K 8/8152* (2013.01); *A61K 8/19* (2013.01); *A61Q 1/10* (2013.01); *A61K 2800/47* (2013.01)

(58) Field of Classification Search
CPC .... A61K 8/8152; A61K 8/19; A61K 2800/47; A61Q 1/10
See application file for complete search history.

(56) References Cited

U.S. PATENT DOCUMENTS

| | | |
|---|---|---|
| 3,516,422 A | 6/1970 | Bechtold et al. |
| 6,325,994 B1 | 12/2001 | Collin et al. |
| 6,326,013 B1 * | 12/2001 | Lemann ............... A61K 8/8147 424/401 |
| 6,458,390 B1 | 10/2002 | Manelski et al. |
| 6,967,024 B2 | 11/2005 | Scancarella et al. |
| 7,601,212 B2 | 10/2009 | Sabesan et al. |
| 8,061,367 B2 | 11/2011 | Rabe et al. |
| 2002/0182409 A1 | 12/2002 | Gueret |
| 2008/0105272 A1 | 5/2008 | Thevenet |
| 2009/0297461 A1 | 12/2009 | Perle et al. |
| 2011/0311597 A1 | 12/2011 | Fleissman et al. |

(Continued)

FOREIGN PATENT DOCUMENTS

| | | |
|---|---|---|
| CN | 106666900 A | 5/2017 |
| CN | 206137315 U | 5/2017 |

(Continued)

OTHER PUBLICATIONS

"Magnetic Eyeliner", Retrieved on Jul. 19, 2018, 5 pages. Available at: https://www.amazon.com/Magnetic-Eyeliner-use-Lashes-Application/dp/B07LB1Q83J/ref=pd_cp_194_1?pd_rd_w=2xhn4&pf_rd_p=ef4dc990-a9ca-4945-ae0b-f8d549198ed6&pf_rd_r=12D13VKCT63CZYV0QM8T&pd_rd_r=933e19b9-098d-11e9-ae91-771b90899601&pd_rd_wg=e6C54&pd_rd_i=B07LB21F7Y&refRID=12D13VKCT63CZYV0QM8T&th=1.

(Continued)

*Primary Examiner* — Kyung S Chang
(74) *Attorney, Agent, or Firm* — Ziegler IP Law Group, LLC

(57) ABSTRACT

Compositions and methods of this disclosure include liquid cosmetic compositions, for example, an eyeliner, that is applied to the surface of a user (e.g., a person), the surface including, for example, an eyelid, the liquid cosmetic product including a ferromagnetic component that is capable of being attracted by and attached to a magnet, the magnet part of a false eyelash.

9 Claims, 1 Drawing Sheet

(56) References Cited

U.S. PATENT DOCUMENTS

| | | |
|---|---|---|
| 2013/0160785 A1 | 6/2013 | Thevenet et al. |
| 2015/0265594 A1* | 9/2015 | Friesen .............. A61K 31/4468 514/282 |
| 2016/0280927 A1 | 9/2016 | Heo et al. |
| 2018/0235299 A1 | 8/2018 | Stoka |
| 2018/0263351 A1 | 9/2018 | Menna et al. |

FOREIGN PATENT DOCUMENTS

| | | |
|---|---|---|
| CN | 106858860 A | 6/2017 |
| CN | 207023344 U | 2/2018 |
| CN | 207322773 U | 5/2018 |
| CN | 207754609 U | 8/2018 |
| CN | 207767606 U | 8/2018 |
| DE | 202017003564 U1 | 9/2017 |
| DE | 202018000679 U1 | 4/2018 |
| EP | 1741363 A1 | 1/2007 |
| JP | H07-324015 A | 12/1995 |
| JP | 2006-160718 A | 6/2006 |
| JP | 200621964 A2 | 10/2006 |
| JP | 3214988 U | 2/2018 |
| KR | 10-2012-0025074 A | 3/2012 |
| KR | 10-2013-0053019 A | 5/2013 |

OTHER PUBLICATIONS

"Magnetic Gel Eyeliner", Retrieved on Jul. 19, 2018, 7 pages. Available at: https://www.moxielash.com/products/magnetic-eyeliner-1.

"Crazy Magnetic Eyelashes Hack! Magnetic Eyeliner?", Retrieved on Jul. 19, 2018, 10 pages. Available at: https://www.youtube.com/watch?v=-6DUfKSHk-o.

PCT, Notification of Transmittal of the International Search Report and the Written Opinion of the International Searching Authority, or the Declaration, Application No. PCT/US20/32298, dated Oct. 23, 2020, 15 pages.

\* cited by examiner

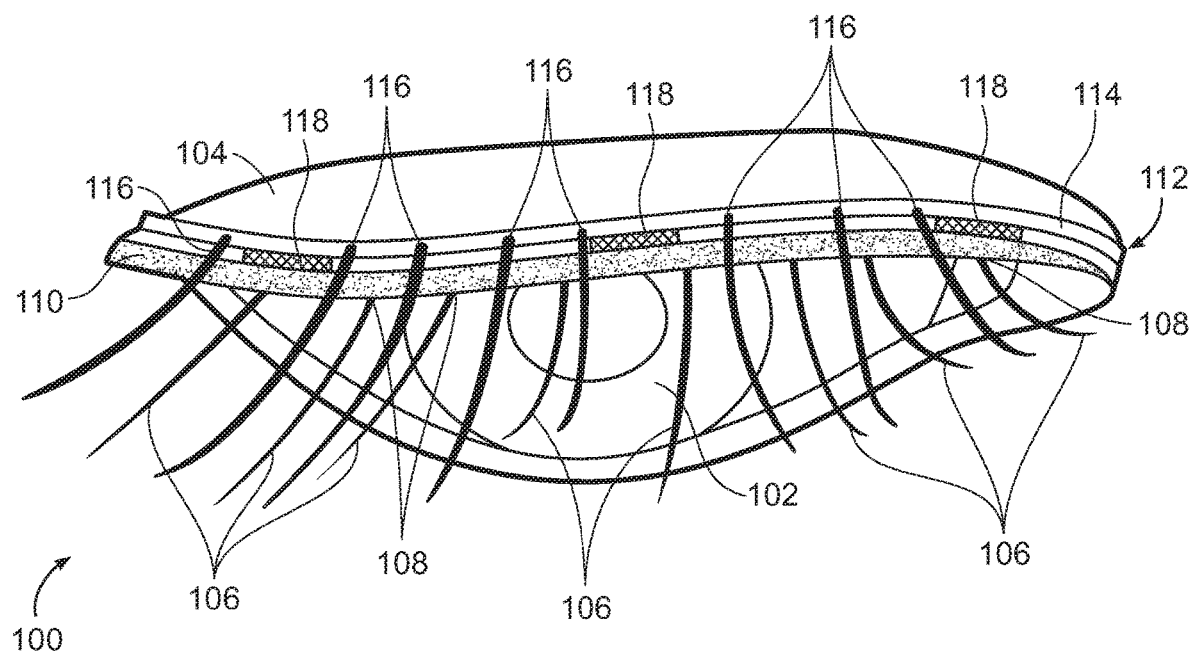

LIQUID COSMETIC

CROSS-REFERENCE TO RELATED APPLICATIONS

This application claims the benefit of priority under 35 U.S.C. § 119(a) to Chinese Patent Application No. 201910393434.5, filed May 13, 2019.

FIELD

The aspects of the disclosed embodiments generally relate to cosmetic products, and in particular compositions and methods related to cosmetic eye products.

BACKGROUND

Eyelashes are a physical feature that people choose to selectively alter in order to improve their appearance. Some will use products, such as mascara, to improve their eyelashes, for example, to make them look thicker and fuller. However, some require even greater enhancement than mere mascara can provide. False eyelashes are an available alternative and can be applied to the wearer's eyelid or eyelash area to enhance the wearer's natural eyelashes.

Current application of false eyelashes can have drawbacks. For example, false eyelashes can be attached using adhesives that are part of the false eyelash itself or a separate adhesive. The latter can be applied to the eyelid area to which the false eyelash is placed in contact and used to affix it to the eyelid. Such adhesives can be irritating to the user and, furthermore, cause discomfort including pain to the wearer when such false eyelashes are forcibly removed.

It would be advantageous to provide a composition and method of use for a cosmetic product, e.g., an eyeliner, that can be applied to the eye lid area and comfortably maintained while being capable of being coupled by magnetic fields to a false eyelash having magnet elements.

SUMMARY

In one embodiment, an eyeliner composition is provided. The eyeliner composition includes a viscosity increasing agent in an amount of from about 15 wt % to about 25 wt % and iron oxide in an amount of from about 25 wt % to about 45 wt %, wherein the composition has a viscosity of from about 950 cps to about 1300 cps at about 25° C.

In another embodiment, a liquid eyeliner composition is provided. The liquid eyeliner composition includes styrene/acrylates copolymer in an amount of from about 15 wt % to about 25 wt % and milled iron oxide in an amount of from about 25 wt % to about 45 wt %, wherein the composition has a viscosity of from about 950 cps to about 1300 cps at about 25° C. and a pH of from about 7.5 to about 8.5.

In another embodiment, a method of attaching a false eyelash to the eyelid of a user using an eyeliner composition is provided. The eyeliner composition includes a viscosity increasing agent in an amount of from about 15 wt % to about 25 wt % and a ferromagnetic component including iron oxide in an amount of from about 25 wt % to about 45 wt %, wherein the composition has a viscosity of from about 950 cps to about 1300 cps at about 25° C. and a pH of from about 7.5 to about 8.5. The false eyelash includes a base including at least one magnet element and false eyelash elements extending from the base. The method includes depositing a portion of the eyeliner composition onto the eyelid or eyelash area of the eyelid and attaching the at least one magnet element of the false eyelash to the deposited portion of the eyeliner composition via the magnet element's attraction and attachment to the ferromagnetic component of the eyeliner composition.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 1 is a schematic illustration of an upper view of an eye and an embodiment of the present disclosure.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

As used herein, "cosmetically-acceptable" means that the components and ingredients which the term describes are suitable for use in contact with tissues (e.g., the skin) without undue toxicity, incompatibility, instability, irritation, allergic response, and the like, commensurate with a reasonable benefit/risk ratio.

The aspects of the present disclosure relates to compositions and methods of use and manufacture of a cosmetic composition, including multi-purpose cosmetic compositions, for example, an eyeliner, including a liquid cosmetic composition, for example, a liquid eyeliner, that is applied to the surface of a user (e.g., a person), the surface including, for example, an eyelid and/or eyelash area, the cosmetic composition including a ferromagnetic component that is capable of being attracted by and attached to a magnet, including a multi-purpose eyeliner that is capable of (1) imparting the cosmetic features of a traditional eyeliner (being applied to the eyelid and/or eyelash area to enhance the appearance thereof) and (2) providing a point of attachment for false eyelashes including magnet elements. The aspects of the present disclosure also relate to compositions and methods of use and manufacture of the present disclosure in combination with eyelash prostheses, e.g., false eyelashes, that include magnet elements as part of the protheses and can be used to attach the false eyelash to the compositions of the present disclosure.

The eyelid area includes the outer surface of the eyelid opposite to the inner eyelid surface adjacent to and/or in contact with the surface of the eye and solutions (natural and artificial) associated therewith (e.g., tears). The eyelid area also includes the surface of the portion of the eyelid from which eyelashes extend or the surface adjacent to that portion from which false eyelashes are capable of being attached without substantially interfering with the opening and closing of the user's eyelid.

A false eyelash includes an eyelash prothesis having a plurality of false eyelash element fibers attached to and extending from a base, the base having a length that can extend along the length of the eyelid area of a user, e.g., the average length of the eyelid area of the average user, or a shorter portion thereof, for example, eyelash extensions. The false eyelash can also include one or more magnet elements, e.g., as part of the structure of or attached to the false eyelash base.

Compositions and methods of the present disclosure include a cosmetic composition, such as an eyeliner, for example, in the form of a liquid, e.g., a liquid eyeliner, that can include a ferromagnetic component that is capable of being attracted to a magnet and a cosmetically acceptable vehicle. The magnet to which the ferromagnetic component is attracted can be a magnet element that is part of the structure of a false eyelash, for example, one or more magnet elements The ferromagnetic component (e.g., a cosmetically acceptable ferromagnetic component) can include ferromagnetic materials and compounds, such as, for example, those including iron (e.g., iron oxides such as Fe2O3 and Fe3O4), nickel, cobalt and some of the rare earths (gadolinium, dysprosium). The ferromagnetic component can include such materials and compounds in the form of particles, but also milled iron oxide that are smaller particles than the unmilled form. The milled form can be made, for example, using a Tri-roller Mill to mill the unmilled iron oxide powder with viscous liquid, such as, for example, water. The ferromagnetic component including iron oxide can act as a colorant for the purpose of making darker shades of eyeliner.

One embodiment of the present disclosure can include a ferromagnetic component, for example, iron oxide (milled or unmilled) in an amount ranging from about 25 wt % to about 45 wt % or about 40 wt % and a cosmetically acceptable vehicle to which the iron oxide is loaded.

The cosmetically acceptable vehicle can include an aqueous based vehicle including a viscosity increasing component (e.g., a cosmetically acceptable viscosity increasing component) such as, for example, polymers (e.g., styrene/acrylates copolymer), magnesium aluminum silicate and gellan gum. The amount of viscosity increasing component can be present in an amount ranging from about 0.5 wt % to about 2.0 wt %) depending on the desired viscosity of the composition. For embodiments of the present disclosure including styrene/acrylates copolymer used as a viscosity increasing component, the styrene/acrylates copolymer can be present in an amount ranging from about 15 wt % to about 25 wt % or about 20 wt %.

Other embodiments of the present disclosure may include various optional ingredients that can include a skin coloring agent, a dispersing agent, a dissolvent, a preservative and a colorant.

A skin coloring agent can change the color of the eyeliner and can include cosmetically acceptable skin coloring agents. Examples of skin coloring agents can include, for example ultramarine (CI 77007) and manganese violet (CI 77742)). A Skin coloring agent can be present in an amount for ultramarine ranging from about 30% to about 40% and for manganese violet ranging from about 3% to about 5%.

A dispersing agent can include cosmetically acceptable dispersing agents. Examples of dispersing agents can include PEG-40 hydrogenated castor oil, polysorbate 20 and sodium stearoyl glutamate. A dispersing agent can be present in an amount ranging from about 0.5 wt % to about 1 wt %.

A dissolvent is volatile which helps the product to dry faster and can include cosmetically acceptable dissolvents. Examples dissolvent s can include denatured alcohol. Dissolvents can be present in an amount ranging from about 1 wt % to about 3 wt %.

A preservative can include cosmetically acceptable preservatives. Examples of preservatives can include phenoxyethanol, ethylhexalglycerin and caprylyl glycol Preservatives can be present in an amount ranging from about 0.5 wt % to about 1 wt %.

An embodiment of the present disclosure is included in FIG. 1. FIG. 1 includes an eye 100, eyeball 102, eyelid 104 and eyelashes 106. The eyelid 104 includes eyelashes 106 that are connected to the eyelid 104 at eyelash connections 108 in an area of the eyelid 104. FIG. 1 also includes a deposit 110 of at least one of the liquid cosmetic compositions and embodiments of the present disclosure. The deposit 110 can be made by making a continuous linear deposit of same (e.g., from one side of an eyelid to the opposite side) or by making several individual or smaller deposits of same such that they are properly positioned to magnetically interact (including one or multiple coats or applications of the composition) and attach to the magnet elements so positioned on a false eyelash and result in the desired positioning of the false eyelash. FIG. 1 also includes a false eyelash 112 with a base 114, false eyelash elements 116 extending from the base 114 and magnet elements 118 connected to the base 114 (of which there can be one or multiple magnet elements, separate or incorporated into the base 114). After the deposit 110 of liquid cosmetic compositions and embodiments of the present disclosure, the false eyelash 112 is placed in contact with the deposit 110 such that the magnet elements 118 attach to the deposit 110 via the magnet element's attraction and attachment to the ferromagnetic component of the composition deposited.

The viscosity of the liquid cosmetic compositions of the present disclosure can be in a range of from about 950 cps to about 1300 cps or about 1100 cps when tested at 25° C. To make the liquid cosmetic compositions properly workable, the viscosity needs to be at a level so that the composition is not too thick so as to adversely impact the application thereof (e.g., too thick to make proper application difficult or to remove from the composition's container), but also not too thin so that the ferromagnetic component (e.g., iron oxide) is not suspended or distributed substantially evenly throughout the composition. Such uneven suspension or distribution of the ferromagnetic component can result in a composition when applied as an eyeliner to which the magnet elements of a false eyelash may not adequately magnetically attach. The pH of the liquid cosmetic compositions of the present disclosure can be in a range of from about 7.5 to about 8.5. A lower pH may adversely affect the viscosity of the liquid cosmetic compositions and embodiments of the present disclosure. As a result, the compositions and embodiments of the present disclosure have several desirable cosmetic and other qualities for the wearer including, but not limited to, a high degree of comfort, ease of application and being long lasting upon application.

Liquid cosmetic compositions and embodiments of the present disclosure may be deposited onto an eyelid area using one or multiple coats or applications of the composition directly from a container of the liquid cosmetic composition or using an acceptable applicator including, for example, an application wand. The application wand can include bristles of various sizes including bristles ranging in size from about 1.2 mm to about 1.4 mm, the large size bristles may pick up more of the liquid cosmetic compositions and embodiments of the present disclosure and be better able to deliver same to the eyelid area with fewer coats or applications. Delivery of the cosmetic compositions and embodiments of the present disclosure can be accomplished (1) by making a continuous linear deposit of same (e.g., from one side of an eyelid to the opposite side) or (2) by making several individual or smaller deposits of same such that they are properly positioned to magnetically interact (both including one or multiple coats or applications of the composition, e.g., from about 1 to about 4) and attach to the magnet elements so positioned on a false eyelash and result in the desired positioning of the false eyelash (both (1) and (2) including one or multiple coats or applications of the composition, e.g., from about 1 to about 4).

Embodiments of the present disclosure may also include combinations of composition embodiments of the present disclosure and a false eyelash in which a composition embodiment of the present disclosure is applied to an eyelid and/or eyelash area of an eyelid and a false eyelash including at least one magnet element is placed in contact with and attached to the composition via the magnet element's attraction and attachment to the ferromagnetic component of the composition. The method of obtaining the combination can include depositing the composition onto an eyelid area and/or eyelash area of an eyelid and attaching a false eyelash including at least one magnet element to the composition via the magnet element's attraction and attachment to the ferromagnetic component of the composition.

Example 1

DI (deionized) water 36.2 wt %; styrene/acrylates copolymer 20.0 wt %; butylene glycol 5.0 wt %; PEG-40 hydrogenated castor oil 2.0 wt %; alcohol denatured 2.0 wt %; phenoxyethanol 0.8 wt %; and iron oxide-milled 35.0 wt %.

Example 2

DI (deionized) water 31.2 wt %; styrene/acrylates copolymer 20.0 wt %; butylene glycol 5.0 wt %; PEG-40 hydrogenated castor oil 2.0 wt %; alcohol denatured 1.0 wt %; phenoxyethanol 0.8 wt %; and iron oxide-milled 40.0 wt %.

Example 3

DI (deionized) water 41.2 wt %; styrene/acrylates copolymer 15.0 wt %; butylene glycol 5.0 wt %; PEG-40 hydrogenated castor oil 2.0 wt %; alcohol denatured 1.0 wt %; phenoxyethanol 0.8 wt %; and iron oxide-milled 35.0 wt %.

Example 4 Assessment of Cosmetic Qualities and Efficacy of Example 2

Checking for skin acceptability—Taking into account the sensations of discomfort felt by no subject and that no subject showed clinical signs ascribable to the test product, the dermatologist classed the product in relation to the grading scale and judged it very well tolerated by the skin. Checking for eye acceptability—Taking into account the sensations of discomfort felt by no subject and that no subject showed clinical signs ascribable to the test product, the ophthalmologist classed the product in relation to the grading scale and judged it very well tolerated by the eye.

Assessment of cosmetic qualities and efficacy.

TABLE 1

| Item | No and % of subjects | | | | |
|---|---|---|---|---|---|
| | Normal | Combination | Oily | Dry | Sensitive |
| What would you say your skin type was? | 4/19% | 11/52% | 1/5% | 4/19% | 1/5% |

TABLE 2

| Item | No and % of subjects | | | | No and % of satisfied subjects |
|---|---|---|---|---|---|
| | Very easy | Quite easy | Not very easy | Not at all easy | |
| Can you tell me how easy the magnetic liner was to apply when you first put it on? | 3/14% | 15/71% | 3/14% | 0/0% | 18/86% |

| Item | No and % of subjects | | | | No and % of satisfied subjects |
|---|---|---|---|---|---|
| | Very comfortable | Quite comfortable | Quite uncomfortable | Very uncomfortable | |
| How did the liner feel on the eye? | 7/33% | 13/62% | 1/5% | 0/0% | 20/95% |

TABLE 3

As stated we would like you to wear this liner for at least 18 hours (the longer the better). Please can you record at what point you took it off? Time (hours)

15
16
15
12
16
10
13-14
13
18
18
14-15
14-15
20-24
13
13
13-15
15
10-12
12
12
8

TABLE 4

| Item | No and % of subjects | | | | No and % of satisfied subjects |
|---|---|---|---|---|---|
| | Strongly agree | Agree | Disagree | Strongly disagree | |
| The liner was smudge-proof. | 5/24% | 15/71% | 1/5% | 0/0% | 20/95% |
| The liner was easy to apply. | 10/48% | 11/52% | 0/0% | 0/0% | 21/100% |
| The liner gave a black solid line. | 13/62% | 7/33% | 1/5% | 0/0% | 20/95% |
| The liner was water-proof (11 subjects concerned). | 6/55% | 5/45% | 0/0% | 0/0% | 11/100% |
| The liner did not flake off. | 12/57% | 7/33% | 2/10% | 0/0% | 19/90% |
| This liner was long-lasting? | 14/67% | 7/33% | 0/0% | 0/0% | 21/100% |
| The liner tested all day. | 14/67% | 7/33% | 0/0% | 0/0% | 21/100% |

TABLE 5

| Item | No and % of subjects | | | | No and % of satisfied subjects |
|---|---|---|---|---|---|
| | Very easy | Quite easy | Not very easy | Not at all easy | |
| Was the liner easy to remove? | 2/10% | 13/62% | 5/24% | 1/5% | 15/71% |

| Item | No and % of subjects | | | | No and % of satisfied subjects |
|---|---|---|---|---|---|
| | Very likely | Quite likely | Not very likely | Not at all likely | |
| How likely would you be to buy this liner in the future? | 10/48% | 5/24% | 6/29% | 0/0% | 15/71% |

| Item | No and % of subjects | | | | No and % of satisfied subjects |
|---|---|---|---|---|---|
| | Strongly Agree | Agree | Disagree | Strongly Disagree | |
| Was this liner a good alternative to your current liner? | 8/38% | 8/38% | 5/24% | 0/0% | 16/76% |

Conclusion—According to the experimental conditions adopted and taking into account the grading scale established by the investigator centre, the product has: a very good skin acceptability; its very good skin tolerance was confirmed; a very good eye acceptability; and its very good eye tolerance was confirmed. Tested under dermatological control and tested under ophthalmological control.

Human repeated insult patch test with challenge of eyeliner adhesive acrylic.

Eyeliner Product Formula:

Study population—Number of test subjects: 50 valid cases. Specific inclusion criteria: test subjects: aged from 18 to 70; female/male; with a phototype (Fitzpatrick): II, III or IV; with all types of skin on body. Specific non-inclusion criteria: test subjects: with personal history of adverse reaction to: ethanol, colophony, rubber, nickel, aluminum, patch materials, adhesive plaster; and with family or personal history of atopy.

Methodology—Application of the investigational product, in healthy human subjects, by a technician, at the investigating centre, to a skin site on the upper back, under maximizing conditions of exposure (under occlusive patch) for a defined time. Repeated applications 9 times to the same site (induction site) over a period of 3 consecutive weeks, period necessary to induce a possible allergy (induction period). After a minimal 2-week rest period, with no product application, single application of the investigational product, under patch, to the induction site and to a virgin site and for a defined time, enabling to reveal a possible induced allergy (challenge). Application in parallel of distilled water under occlusive patch at the same defined times as the investigational product=control site. Skin examination of the application site, before the 1st product application of the induction period and the application of the challenge phase and after each patch removal by the same investigator or technician, supervised by the investigator. Reporting of the sensations of discomfort directly by the test subjects to the investigator or technician, during the study. Assessment of the allergic potential—checking of the skin compatibility: accurate description of the skin reactions observed; evaluation of the allergic reaction according to the ICDRG scale: ?+, (+), (++), (+++); calculation of the percentage of reactive test subjects during the challenge phase and the induction period.

Characteristics of the included panel—Number of included subjects: 52; Number of exclusions: none; Number of withdrawals: (reason): 2 (ref. 16b and 36b)—for personal reasons independent from the study; Number of valid cases: 50; Age: 25 to 70 (Mean: 47); Sex: F/M; Phototype: II and III; and Skin types on the application site: with all types of skin on body.

Checking of the skin compatibility—No reaction was noted on the control site.

Induction period—Type of reaction (E: Erythema; M: complementary mention and A: ICDRG scale), For all, Description of the reaction on the induction site—None; Number and percentage of reactive test subjects—0/0%; and Total number and percentage of reactive test subjects—0/0%.

Challenge phase—Type of reaction (E: Erythema; M: complementary mention and A: ICDRG scale), For all, Description of the reaction on the induction site and the virgin site—None; Number and percentage of reactive test subjects—0/0%; and Total number and percentage of reactive test subjects—0/0%.

Conclusion—Under the experimental conditions adopted: During the induction period, the repeated applications of the product, under occlusive patch, on a panel of 50 test subjects with all types of skin on body, induced no reaction of irritation; During the challenge phase, the single application of the investigational product to the induction site and virgin site induced no allergic reaction. Based on these results, the product has a very good skin compatibility and does not show a sensitizing effect.

Human repeated insult patch test with challenge of eyeliner adhesive latex.

Eyeliner Product Formula:

Study population—Number of test subjects: 50 valid cases. Specific inclusion criteria: test subjects: aged from 18 to 70; female/male; with a phototype (Fitzpatrick): II, III or IV; with all types of skin on body. Specific non-inclusion criteria: test subjects: with personal history of adverse reaction to: ethanol, colophony, rubber, nickel, aluminum, patch materials, adhesive plaster; and with family or personal history of atopy.

Methodology—Application of the investigational product, in healthy human subjects, by a technician, at the investigating centre, to a skin site on the upper back, under maximizing conditions of exposure (under occlusive patch) for a defined time. Repeated applications 9 times to the same site (induction site) over a period of 3 consecutive weeks, period necessary to induce a possible allergy (induction period). After a minimal 2-week rest period, with no product application, single application of the investigational product, under patch, to the induction site and to a virgin site and for a defined time, enabling to reveal a possible induced allergy (challenge). Application in parallel of distilled water under occlusive patch at the same defined times as the investigational product=control site. Skin examination of the application site, before the 1st product application of the induction period and the application of the challenge phase and after each patch removal by the same investigator or technician, supervised by the investigator. Reporting of the sensations of discomfort directly by the test subjects to the investigator or technician, during the study. Assessment of the allergic potential—checking of the skin compatibility: accurate description of the skin reactions observed; evaluation of the allergic reaction according to the ICDRG scale: ?+, (+), (++), (+++); calculation of the percentage of reactive test subjects during the challenge phase and the induction period.

Characteristics of the included panel—Number of included subjects: 52; Number of exclusions: none; Number of withdrawals: (reason): 2 (ref. 3b and 31a)—for personal reasons independent from the study; Number of valid cases: 50; Age: 20 to 61 (Mean: 48); Sex: F/M; Phototype: II and III; and Skin types on the application site: with all types of skin on body.

Checking of the skin compatibility—No reaction was noted on the control site.

Induction period—Type of reaction (E: Erythema; M: complementary mention and A: ICDRG scale), For all, Description of the reaction on the induction site—None; Number and percentage of reactive test subjects—0/0%; and Total number and percentage of reactive test subjects—0/0%.

Challenge phase—Type of reaction (E: Erythema; M: complementary mention and A: ICDRG scale), For all, Description of the reaction on the induction site and the virgin site—None; Number and percentage of reactive test subjects—0/0%; and Total number and percentage of reactive test subjects—0/0%.

Conclusion—Under the experimental conditions adopted: During the induction period, the repeated applications of the product, under occlusive patch, on a panel of 50 test subjects with all types of skin on body, induced no reaction of irritation; During the challenge phase, the single application of the investigational product to the induction site and virgin site induced no allergic reaction. Based on these results, the product has a very good skin compatibility and does not show a sensitizing effect.

Microbiological Tests.

Eyeliner Product Formula:

Method description: the evaluation of the preservation of a cosmetic formulation is based on inoculation of the formulation with calibrated inoculum ($10^7$-$10^8$ for bacteria and $10^6$-$10^7$ for yeasts and moulds). After contamination, the sample is left for a period of 28 days, the contact time is a preservative with the introduced microorganism in the environment of the product. At intervals of 7, 14, 28 the sample plated on and based on the results the log reduction value is calculated and compared to the minimum values required for evaluation criterion A or B in the standard. Tested microorganisms: *Pseudommonas aeruginosa* ATCC9027, *Escherichia coli* ATCC8739, *Staphylococcus aureus* ATCC6538, *Candida albicans* ATCC10231 and *Aspergillus brasiliensis* (*niger*) ATCC16404 (spores). Used media, diluents, neutralizers: sodium chloride solution, polysorbate solution, tryptic soy agar, sabouraud, agar with potato dextrose, water 1000 ml. and neutralizer eugon LT100. Composition: pancreatic digest of casein 15.0 g, papaic digest of soybean meal 5.0 g, sodium chloride 4.0 g, L-sytine 0.7 g., sodium sulphite 0.2 g, blucose 5.5 g, egg lecithin 1.0 g, polysorbate 80 5.0 g, octoxynol 9 1.0 g and water 1000 ml. Sample incubation for 28 days at 22.5+/−2.5° C. Bacteria and yeasts for 72 h at 32.5+/−2.5° C. Moulds for 72 h at 22.5+/−2.5° C.

TABLE 6

| Tested microorganisms | Nvf | Nvn | Nv | Nvf ≥ 0.5 Nvn* | The efficacy of the neutralizer is demonstrated |
|---|---|---|---|---|---|
| E. coli | 26 cfu/ml | 16 cfu/ml | 36 cfu/ml | 26 ≥ 8 | + |
| S. aureus | 27 cfu/ml | 20 cfu/ml | 47 cfu/ml | 27 ≥ 10 | + |
| Ps. aerginosa | 32 cfu/ml | 28 cfu/ml | 47 cfu/ml | 32 ≥ 14 | + |
| C. albicans | 37 cfu/ml | 22 cfu/ml | 57 cfu/ml | 37 ≥ 11 | + |
| A. brasiliensis | 20 cfu/ml | 19 cfu/ml | 21 cfu/ml | 20 ≥ 10 | + |

The neutralizer efficiency based on demonstration of the neutralizer efficiency, results are accordance with criteria, for all microorganisms: *Pseudommonas aeruginosa* ATCC9027, *Escherichia coli* ATCC8739, *Candida albicans* ATCC10231 and *Aspergillus brasiliensis*.

Nvf-enumeration cfu/ml in a mixture of the neutralizer and the formuation, Nvn-enumeration cfu/ml in a mixture of the neutralizer and the diluent, Nv=enumeration cfu/ml in a control. The efficacy of the neutralizer is demonstrated if Nvf0.5Nvm abdif Nvn is close to Nv. If Nvn is not close to Nv; 1/10, 1/100 dilution of formulation.

TABLE 7

| | | | Calculations N = C/(Vxd) N0 = N/100 Nx = C/(Vxd) | | | | | | |
|---|---|---|---|---|---|---|---|---|---|
| Tested microorganisms | N- the number of micro-organisms present in the calibrated suspensions | N0 - the number of micro-organisms inoculated in the formulation at time t0 | | Test results | | | | | |
| | | | | T7 | | T14 | | T28 | |
| E. coli | $3.9*10^7$ cfu/ml | $3.9*10^5$ cfu/ml | 5.6 log | Nx = 900 cfu/g | 3.0 log | Nx = <10 cfu/g | 1.0 log | Nx = <10 cfu/g | 1.0 log |
| S. aureus | $4.4*10^7$ cfu/ml | $4.4*10^5$ cfu/ml | 5.6 log | Nx = 330 cfu/g | 2.5 log | Nx = <10 jtk/g | 1.0 log | Nx = <10 cfu/g | 1.0 log |
| Ps. aeruginosa | $4.7*10^7$ cfu/ml | $4.7*10^5$ cfu/ml | 5.7 log | Nx = 430 cfu/g | 2.6 log | Nx = <10 cfu/g | 1.0 log | Nx = <10 cfu/g | 1.0 log |
| C. albicans | $6.7*10^6$ cfu/ml | $6.7*10^4$ cfu/ml | 4.8 log | Nx = <10 cfu/g | 1.0 log | Nx = <10 cfu/g | 1.0 log | Nx = <10 cfu/g | 1.0 log |
| A. brasiliensis | $1.5*10^6$ cfu/ml | $1.5*10^4$ cfu/ml | 4.2 log | — | | Nx = 3000 cfu/g | 3.5 log | Nx = <10 cfu/g | 1.0 log |

Nx—the number of surviving micro-organisms in the contaminated formulation, in colony-forming units per milliliter or grams, at each sampling time, tx, (T7, T14 or T28), T-time of incubation.

TABLE 8

$Rx = \log N0 - \log Nx$
Cosmetic product complies criterion A, because:

| | Criteria | | | Results | | | The log reduction value complies criteria A |
|---|---|---|---|---|---|---|---|
| | | | | Research date 26 Mar. 2019 | Research date 2 Apr. 2019 | Research date 16 Apr. 2019 | |
| Micro-organism | T7 | T14 | T28 | T7 | T14 | T28 | |
| *Escherichia coli* | R7 ≥ 3 | R14 ≥ 3 i NI | R28 ≥ 3 i NI | Rx = 2.6 ≥ 3* | Rx = 4.6 ≥ 3 i NI | Rx = 4.6 ≥ 3 i NI | + |
| *Staphylococcus aureus* | R7 ≥ 3 | R14 ≥ 3 i NI | R28 ≥ 3 i NI | Rx = 3.1 ≥ 3 | Rx = 4.6 ≥ 3 i NI | Rx = 4.6 ≥ 3 i NI | + |
| *Pseudomonas aeruginosa* | R7 ≥ 3 | R14 ≥ 3 i NI | R28 ≥ 3 i NI | Rx = 3.1 ≥ 3 | Rx = 4.7 ≥ 3 i NI | Rx = 4.7 ≥ 3 i NI | + |
| *Candida albicans* | R7 ≥ 1 | R14 ≥ 1 i NI | R28 ≥ 1 i NI | Rx = 3.8 ≥ 1 | Rx = 3.8 ≥ 1 i NI | Rx = 3.8 ≥ 1 i NI | + |
| *Aspergillus brasiliensis* | — | R14 ≥ 0 | R28 ≥ 1 i NI | — | Rx = 0.7 ≥ 0 | Rx = 3.2 ≥ 1 i NI | + |

Rx—the reduction values, Rx expressed in log units, obtained at each sampling time T7, 114, T28, NI-no increase in the count from the previous contact time. According to the standard permissible deviation from the value 0.5 of a log unit.

TABLE 9

Test results
1. Microbiological quality of the product:

| Parametr | Test results | Unit |
|---|---|---|
| Enumeration of aerobic mesophilic bacteria PN-EN ISO 21149: 2017-07 | <10 | cfu/g |
| Enumeration of molds and yeast PN-EN ISO 16212: 2017-08 | <10 | cfu/g |
| Detection of specified (*Pseudomonas aeroginosa, Escherichia coli, Staphylococcus aureus, Candida albicans*) and non-specified microorganisms PN-EN ISO 18415: 2017-07 | Absent of aerobic mesophilic organisms (specified microorganisms included) | 0.1 g |

TABLE 10

Results of Analysis
Microbiological Test Results:

| Aerobic Mesophilic Bacteria | <10 cfu/g |
|---|---|
| Yeast & Mould | <10 cfu/g |
| *Pseudomonas aeruginosa* | Not detected/0.1 g |
| *Staphylococcus aureus* | Not detected/0.1 g |
| *Escherichia coli* | Not detected/0.1 g |
| *Candida albicans* | Not detected/0.1 g |

Key:
cfu/g = Colony Forming Units per gram
< = Less than
Aerobic Mesophilic Bacteria method based on ISO 21149: 2017-07
Yeast & Mould method based on ISO 16212: 2017-08
Defection of *Pseudomonas aeruginosa* - BS ISO 22717: 2016
Detection of *Staphylococcus aureus* - BS ISO 22718: 2016
Detection of *Candida albicans* - BS ISO 18416: 2009
Detection of *Escherichia coli* - BS ISO 21150: 2010

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A liquid eyeliner composition, comprising:
   a. a cosmetically-acceptable styrene/acrylates copolymer in an amount of from about 15 wt % to about 25 wt %; and
   b. a cosmetically-acceptable milled iron oxide in an amount of from about 35 wt % to about 45 wt % sufficient to being attracted by and attached to a magnet and wherein a point of attachment for a false eyelash including a magnetic element is provided,
      i. wherein the composition has a viscosity of from about 950 cps to about 1300 cps at about 25° C. and a pH of from about 7.5 to about 8.5.

2. The liquid eyeliner composition of claim 1, wherein the styrene/acrylates copolymer is present in an amount of about 20 wt %.

3. The liquid eyeliner composition of claim 1, wherein the milled iron oxide is present in an amount of about 40 wt %.

4. The liquid eyeliner composition of claim 1, wherein the composition has a viscosity of about 1100 cps at about 25° C.

5. A method of attaching a false eyelash to the eyelid of a user using the eyeliner composition according to claim 1, the false eyelash comprising:

a. a base including at least one magnet element; and
b. false eyelash elements extending from the base, and the eyeliner composition, the method comprising:
      i. depositing a portion of the eyeliner composition onto the eyelid or eyelash area of the eyelid; and
      ii. attaching the at least one magnet element of the false eyelash to the deposited portion of the eyeliner composition via the magnet element's attraction and attachment to the ferromagnetic component of the eyeliner composition.

6. The method of claim 5, wherein the styrene/acrylates copolymer is present in an amount of about 20 wt %.

7. The method of claim 5, wherein the iron oxide is present in an amount of about 40 wt %.

8. The method of claim 5, wherein the milled iron oxide is present in an amount of about 40 wt %.

9. The method of claim 5, wherein the composition has a viscosity of about 1100 cps at about 25° C.

\* \* \* \* \*